United States Patent [19]

Dearing, Jr.

[11] Patent Number: 5,345,819
[45] Date of Patent: Sep. 13, 1994

[54] METHOD AND APPARATUS FOR WELLBORE STABILITY ANALYSIS

[75] Inventor: Harry L. Dearing, Jr., Sugar Land, Tex.

[73] Assignee: Chevron Research and Technology Company, San Francisco, Calif.

[21] Appl. No.: 601,960

[22] Filed: Oct. 22, 1990

[51] Int. Cl.$^5$ ............................................. E21B 49/00
[52] U.S. Cl. ..................................... 73/153; 166/250; 175/50; 73/788
[58] Field of Search ............................ 175/50; 166/250; 73/153, 38, 151, 152, 155, 788, 794, 796, 798

[56] References Cited

U.S. PATENT DOCUMENTS

| | | | |
|---|---|---|---|
| 2,531,083 | 11/1950 | Smith | 73/153 |
| 3,139,747 | 7/1964 | Ferrell et al. | 73/38 |
| 4,380,930 | 4/1983 | Podhrasky et al. | 73/594 |
| 4,486,714 | 12/1984 | Davis et al. | 73/153 |
| 4,487,056 | 12/1984 | Wiley | 73/38 |
| 4,561,289 | 12/1985 | Jones | 73/38 |
| 4,753,107 | 6/1988 | Reed et al. | 73/38 |
| 4,907,448 | 3/1990 | Givens | 73/38 |
| 5,025,668 | 6/1991 | Sarda et al. | 73/795 |
| 5,069,065 | 12/1991 | Sprunt et al. | 73/38 |

OTHER PUBLICATIONS

Steiger et al., "Quantitative Determination of the Mechanical Properties of Shales", SPE publication No. 18024, Oct. 2, 1988, pp. 69–76.
Steiger et al., "Predictions of Wellbore Stability in Shale Formations at Great Depth," in *Rock at Great Depth*, Maury & Fourmaintraux, (eds.), vol. 3, Aug. 28, 1989.

*Primary Examiner*—Hezron E. Williams
*Assistant Examiner*—George M. Dombroske
*Attorney, Agent, or Firm*—W. K. Turner; M. W. Carson

[57] ABSTRACT

Method and apparatus for the nondestructive testing of rock samples as a function of time are disclosed. A rock sample is placed in a sample vessel which simulates in-situ wellbore conditions of pressure, temperature and fluid effects. Ultrasonic signals are transmitted through the sample and the transit time is measured. The measurements are repetitively performed and the time history of the development of strength is recorded in order to determine when the rock sample begins to weaken.

8 Claims, 3 Drawing Sheets

SAMPLE VESSEL

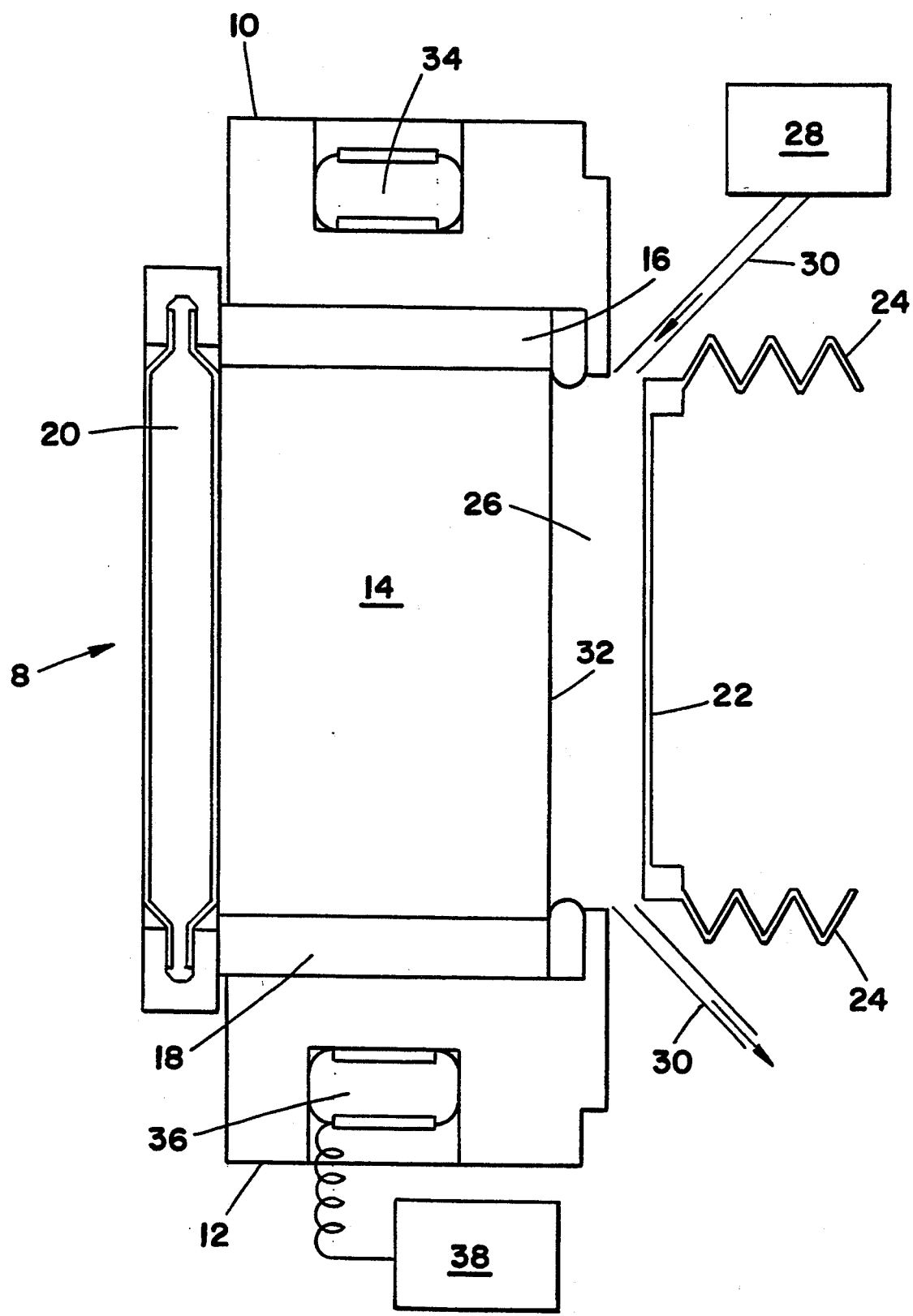
SAMPLE VESSEL
FIG_1

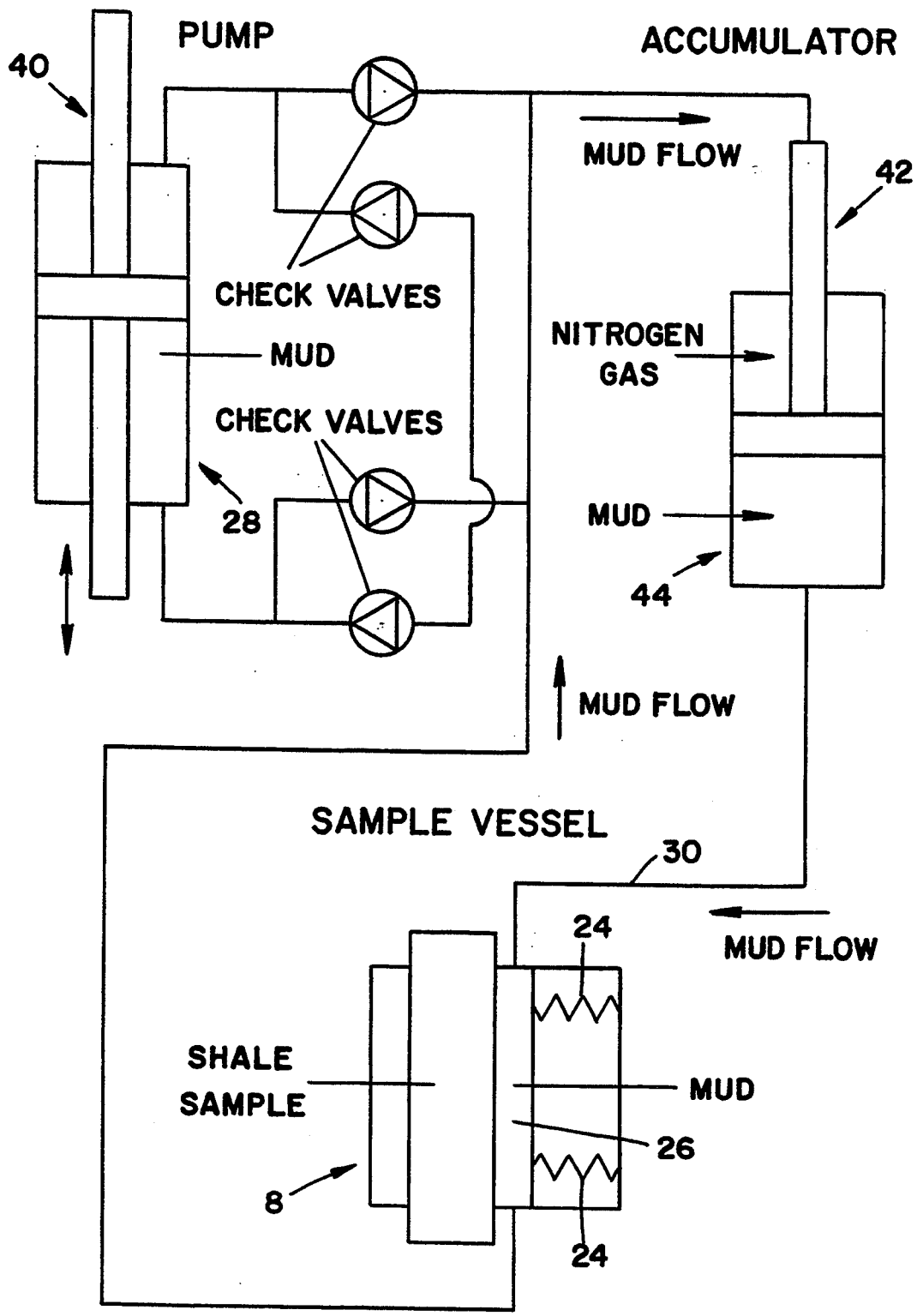
FIG_2

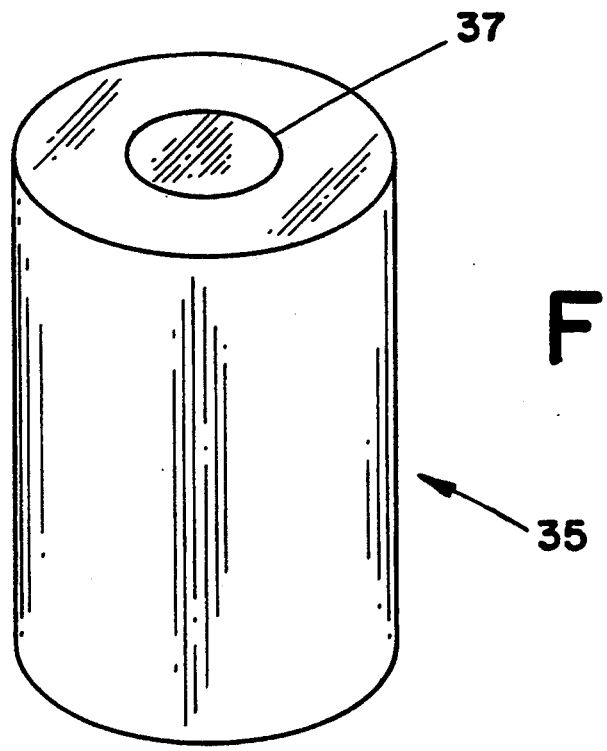
FIG_3A
HOLLOW CYLINDER SAMPLE
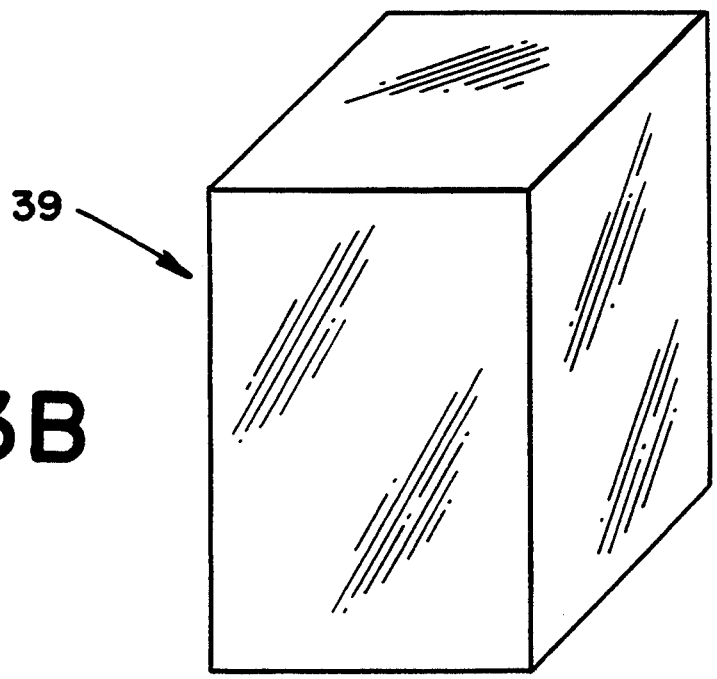
FIG_3B
PRISMATIC SAMPLE

METHOD AND APPARATUS FOR WELLBORE STABILITY ANALYSIS

BACKGROUND OF THE INVENTION

Wellbore stability problems are common in the drilling of oil and gas wells. Wellbore instability is indicated when a wellbore collapses causing pipe sticking, when unstable formations slough cavings into the wellbore, or when a wellbore excessively enlarges. The formations that usually cause wellbore instability are shale and mudstone. A shale is a relatively impermeable formation that contains compacted fine grain sediments and reactive clays. Usually, shale formations are low strength, plastically deformable rocks that are reactive to drilling fluids.

Shale formation evaluation has historically been to identify the types and amounts of clays in the formation, to gauge the degree of dispersion of unstressed cuttings when exposed to mud, and to measure the unstressed swelling of the shale when exposed to fluids. These evaluation techniques fail to consider any rock mechanical properties, and therefore, have not proven to be very effective in predicting wellbore stability or as aides for choosing drilling muds that prevent or delay wellbore destabilization.

The triaxial compression test is the most common test method used to investigate rock mechanical properties. In the triaxial test, a jacketed cylindrical rock sample is axially loaded while a confining pressure is applied. In many cases the testing is made without provision to control rock pore fluid pressure, this is described as undrained tests. When pore fluid pressure is measured and controlled, the test is considered a drained test. Typically, the axial load is compressive and increased while holding the confining pressure constant until the rock sample reaches some maximum axial distortion. Determination of rock mechanical properties using triaxial apparatus in drained and undrained modes is commonplace in mining and excavating activities.

In the conventional triaxial test and in most analyses of rock stresses, the force components of the loading on the rock specimen are resolved into three principal components, $\sigma_1$, $\sigma_2$, and $\sigma_3$, with $\sigma_1 \geq \sigma_2 \geq \sigma_3$. In the triaxial test, $\sigma_1$, the greatest principal stress is the axial load and $\sigma_2$, the intermediate principal stress, equal to $\sigma_3$, the least principal stress, and applied by confining pressure. The confining pressure is a hydraulic pressure provided by a hydraulic fluid such as oil or water inside the test cell. Most of the testing done to date has been related to determining a maximum axial stress (or $\sigma_1$) achieved under test conditions. This value is generally considered the compressive strength of the material. Another test method that utilizes more complicated means of applying strains and stresses is called the polyaxial test. Square cross section rectangular rock specimens are loaded axially as in the triaxial test, but, instead of a confining pressure, a system of four flat-jacks or a system of pistons provide lateral restraint. Using apparatus like these, values of intermediate principal stress greater than the least principal stress are possible. Analysis of test results for both the triaxial test and the polyaxial test is simplified by the application of homogeneous stresses to the sample.

The current method for determining well bore stability is to obtain shale samples from downhole cores or surface outcroppings, determine the mechanical properties of the sample with a series of triaxial tests, estimate the downhole stresses and calculate the maximum stress level that allows the wellbore to remain stable. The calculation method used for this will be based on some yield criterion. As described in G. F. Fuh's "Use of Borehole Stability Analysis for Successful Drilling of High-Angle Hole", the most widely used stability criteria is called the Extended Von Mises yield criteria. This mechanical approach to the stabilization of wellbores will probably fail in many situations.

This has proven inadequate because a number of areas where the triaxial tests may be misleading when related to wellbore stability have been identified. They fall into two categories. The first category relates to mechanical factors and their incompatibility with a drilling wellbore. These factors include the geometry of the test, the loading path and strain rate for the test, and the destructive nature of the test. The second category relates to the drilling fluid and the effects of exposure on the rock properties under downhole stress conditions. These factors include the hydration of the clay containing shale when exposed to drilling fluids, osmotic effects that may cause formation strengthening or weakening, cation exchanged phenomena that may alter the strain behavior, and chemical alteration from alkali that can prevent or promote rock failure.

The failure characteristics of many materials can depend on the order and timing of stress application. Field experience and laboratory testing to date indicates that shale is one of these materials that is load path dependent. Post failure properties are even more load path dependent than the failure characteristics with sedimentary rocks. In almost all cases of wellbore instability, the evidence of failure is not immediate, but occurs days, weeks, or even months after the wellbore is drilled and prior to running of casing. This suggests that the failure of the rock occurs after a long period of time under a high stress level. Conventional testing cannot re-create these long periods at high stress levels because the rock fails quickly in a conventional triaxial test under steadily increasing axial stress at high strain rates. Using a constant stress level over a long period of time is not practical as it would effectively keep expensive test equipment occupied for a prolonged period, unacceptably reducing equipment throughput. Also, since most rock weakening occurs with exposure to drilling fluids, conventional equipment (triaxial and polyaxial test cells) would not determine fluid effects.

Both of the test methods discussed to this point, triaxial testing and polyaxial testing, rely on sample failure to determine the ultimate strength of the rock. Changes in the rock with different confining stresses cannot be gauged without the stressing of the rock to a failure point. This sort of testing requires that many samples be tested to explore the rock failure "envelope" for a particular rock sample. With most plastic rocks like the shales, a minimum of two triaxial tests are required to adequately describe the rock failure mechanism. If long term loading effects and the effect of intermediate principal stress are also to be gauged, a long term research project is probably required. Large scale research projects, aside from being costly, are not practical in a field service environment and certainly are not desirable situations for someone trying to drill a troublesome shale.

The destructive nature of these tests poses interesting questions when interpretation of the results is needed. This is particularly true when the results are to be used to gauge the stability of a wellbore. Information from mining and excavation processes indicates that proper support of failed rock can produce a stable excavation, even with the strength of the material exceeded in portions of the rock body. The fact is that shear failure of rock surrounding a wellbore does not imply that wellbore is unstable. Determining if failed rock can support enough of the rock stresses requires a geometry more comparable to the wellbore than the conventional tests.

Hydration of clays that exist within the shale matrix are felt to increase the effective stress on the shale body. These increases in effective stress can reduce the strength of a shale and cause it to fail. The quantification of hydration effects is particularly difficult as the effects are dependent on the previous stress state and current stress state. Exposure of shale to in situ stress levels and drilling fluid is the most applicable method assess hydration effects. One approach used today has been to triaxially stress a shale sample and drill in with a mud.

Related to hydrational stresses, osmotic effects reflect the different salts and salt concentration present in the drilling fluid and shale. When the salt concentration between the mud and the shale is different, and osmotic pressure exists that can cause fluid diffusion from the shale into the mud. This diffusion can help destabilize a wellbore. Primary osmotic effects are not stress related, but secondary osmotic effects from hydrational pressures can be significant.

Clays occur with charge deficiencies within their crystalline structure that encourages the adsorption of cations like sodium (Na+), potassium (K+), and calcium (Ca++). Under the right conditions of temperature, stress, and concentration, the clay's existing adsorbed cations can be displaced by another species of cation. This can cause the clay to change properties and will affect the properties of a shale containing these clays.

The chemistry of a mud can have a profound effect on the fabric of a shale. Alkali in the mud can cause the weakening of the shale or can alter it to form a stronger material. The presence of clay dispersants and deflocculants can cause softening of the wellbore surface. Chemical alteration and shale stability should be determined at downhole conditions. Chemical alteration effects can be much different for shale in an unstressed state compared to effects in a stressed state.

Heretofore, many processes have been utilized in attempting to test shale under conditions of near downhole stress. Polyaxial and triaxial compression tests have been attempted. However, these methods have not been overly successful because they fail to consider rock mechanical properties and the effects to the sample because of conditions of downhole stress and pore pressure with exposure to drilling fluid at in situ temperature and pressure. There is therefore a need for an improved apparatus and method of evaluating rock properties under downhole conditions that is easy and cost effective to conduct.

SUMMARY OF THE INVENTION

The present invention is directed to an apparatus and method of evaluating the effects of drilling fluids, rock stresses, and stress variations on rock properties under downhole stress conditions. This invention is directed towards an apparatus and method which evaluates fluids for wellbore stability with rock stresses that would be the same as those found at a depth in a drilling oil or gas well. A means for monitoring the fluid effects on shale properties is used to avoid the destructive nature of conventional rock properties measurement using ultrasonic transit velocities.

OBJECTS OF THE INVENTION

The principle object of the present invention is to evaluate rock formations under conditions of near downhole stress and pore pressure with exposure to drilling fluid at in-situ temperature and pressure. The fluid effects are measured using ultrasonic transit velocities as a means to avoid the destructive nature of conventional rock properties measurement. Another object of this invention is to improve the accuracy of the measurement taken to determine time dependent behavior of the rock sample while preserving substantially the same shape of the rock sample. Further objects and advantages of the present invention will become apparent when the description is read in view of the accompanying drawings which are made part of this specification.

BRIEF DESCRIPTION OF DRAWINGS

FIG. 1 is a cross sectional view of an apparatus assembled in accordance with the present invention.

FIG. 2 is a schematic block diagram illustrating an embodiment of the present invention.

FIG. 3A shows a side and top view of a rock sample used in accordance with conventional stability testing.

FIG. 3B shows a top and side view of a rock sample used in accordance with the present invention.

DETAILED DESCRIPTION OF THE INVENTION

The nondestructive testing apparatus of the present invention is based upon measurement of the time travel of an ultrasonic signal coupled through a rock sample whose characteristics are to be measured. An accurate generalized relationship for relating the compressive strength of rock samples to the travel time of ultrasonic signals therethrough has been developed. A method and apparatus for accurately measuring the change in transit time through a rock sample over a period of time, while the sample is exposed to in-situ temperature, pressure and drilling fluids, and thereby compiling a record of its strength history is provided in the present invention.

Referring initially to FIG. 1, the sample vessel 8 of the present invention is illustrated. FIG. 1 shows a pair of spaced-apart platens 10 and 12, for applying axial stress/strain to a rock sample 14. Platen 10 is termed the top platen and platen 12 is termed the bottom platen. Two porous plates, 16 and 18, are located between said platens 10 and 12 and said rock sample 14. The porous plates 16 and 18 are used to control pore pressure.

A flat jack 20 is located along one side of said rock sample 14 and perpendicular and adjacent to the same ends of said porous plates, 16 and 18 and the top and bottom platen, 10 and 12. The flat jack 20 is used to aid in the confinement of the rock sample 14.

A retractable fluid exposure plate 22 is along the rock sample 14 and opposite the flat jack 20. The retractable fluid exposure plate 22 is attached to bellows 24 (shown partially retracted) which allow the retractable fluid exposure plate 22 to be moved further or nearer to the rock sample 14. As the retractable fluid exposure plate 22 is moved further from the rock sample 14 by the bellows 24, a fluid flow path 26 is created. Drilling fluids are flowed from a drilling fluid source 28 through appropriate piping and fittings 30 and alongside a face of the rock sample 32 to expose the sample 14 to the effects of downhole drilling fluids. The retractable fluid exposure plate 22 is controlled by the bellows 24 to increase or decrease the size of the drilling fluid flow path 26.

In operation it is usually desirable to first introduce a rock sample 14 into the sample vessel 8 and apply axial stress/strain and pore pressure from the top platen 10, bottom platen 12 and porous plates 16 and 18. The flat jack 20 helps to hold the sample 14 in confinement. At this time, the retractable fluid exposure plate 22 is held in position against the sample 14. When sufficient pressure is established, meaning an axial load of 1,000–10,000 psi and a confining stress of 500–9,000 psi, the bellows 24 are then retracted. Drilling fluid is flowed from the drilling fluid source 28 past the exposed face of the sample 32. The pressure and drilling fluid are used to simulate downhole conditions.

The drilling fluid flowing through the drilling fluid flow path 26 and along the exposed wall of the rock sample 14 can be mud, cement, completion fluids or many others known in the art.

The rock sample 14 used in the sample vessel 8 may be sandstone, mudstone, shale, dolomite, limestone and many others known in the art. In the preferred embodiment, the sample is shale. The geometry of the sample is very important. As can be seen in FIG. 3A, conventional samples 35 were cylindrical with a core 37 running through them. Fluid would be run through the core for many hours, days or weeks, whatever was necessary for it to fail. However, as previously discussed, this method was not useful for determining time dependent behavior of the sample. The present invention employs a prismatic-shaped sample 39 as seen in FIG. 3B. This sample better depicts a portion of the wellbore. Drilling fluid is found to run alongside one face 32 of a shale sample 14 as it does in a wellbore. The dimensions of the prism should be large enough to portray a shale matrix. Other advantages of using a prismatic-shaped sample are that smaller samples may be used and the elimination of the troublesome drilling of a cylindrical sample with a miniature drill bit to produce the core, through which drilling fluid is flowed.

The drilling fluid source 28, in this example as shown in FIG. 2, comprises a drilling fluid circulating system having a piston pump 40, accumulator 42 and pressurization means 44. The design of such a system should allow for the operation of the equipment at temperatures to 400° F. and drilling fluid pressures of up to at least 10,000 psi.

Referring back to FIG. 1, the top and bottom platens, 10 and 12, act as housing for ultrasonic transducers 34 and 36. Ultrasonic transducer 34 is housed in top platen 10 and ultrasonic transducer 36 is housed in bottom platen 12. When the ultrasonic transducer 34 is activated a signal waveform is transmitted through the rock sample 14 and received by the ultrasonic transducer 36. From the receiver transducer 36 a signal analogous to the signal received from ultrasonic transducer 34 is supplied to a recorder 38. The recorder 38 precedes to record a series of said signals. These signals are then compared to a generalized relationship, which has already been created, of the strength of rock samples to the change in transit time of the ultrasonic signal sent to establish the strength of the rock sample 14, present in the sample vessel 8.

In another embodiment, the results of the testing on a particular sample may be plotted on a digital plotter. A compressure strength versus transit time as a function of time curve can then be drawn. These curves will then very accurately portray at what exact time the sample begins to weaken.

The rock sample 14 is then removed from the sample vessel 8 in substantially the same state that it was first installed. The present invention is non-destructive, thus the sample may be reused. Moreover, the cost of coring another sample is eliminated.

The foregoing description may make other alternative arrangements according to the concepts of the invention apparent to those skilled in the art. It is therefore the aim of the appended claims to cover all such changes and modifications as fall within the true spirit and scope of the invention.

What is claimed is:

1. An apparatus for determining wellbore stability comprising:
   a. means for housing a prismatic shaped rock sample and for controlling the pressure and temperature of the sample, and means for exposing a face of said sample that is not subject to axial loading to a drilling fluid;
   b. means for generating an ultrasonic signal coupled to said rock sample;
   c. means for measuring the transit time of said ultrasonic signal to travel through said rock sample over a period of time and for generating a measurement signal representative thereof while said sample is exposed to said drilling fluid; and
   d. means, responsive to said measurement signal, for generating according to a predetermined relationship relating said transit time to strength, a signal representative of said strength of said rock sample.

2. The apparatus of claim 1 and further comprising;
   a. control means for controlling said means for generating said ultrasonic signal and said measurement means to repetitively perform measurements of transit time and strength; and
   b. means for recording said repetitive measurements of said strength representative signal as a function of time, thereby to provide a time history of the strength of said rock sample.

3. The apparatus of claim 1 wherein said means for generating an ultrasonic signal through the rock sample comprises ultrasonic transducers on opposite sides of said sample.

4. A method for non-destructively measuring the strength of a rock sample having at least one face, comprising the steps of:
   a. maintaining a rock sample at a controlled temperature and pressure and passing a drilling fluid over one face of said sample;
   b. transmitting an ultrasonic signal through the sample;
   c. detecting said ultrasonic signal subsequent to its transiting the sample and measuring the time required for said signal to transit the sample; and
   d. determining, according to a predetermined relationship relating transit time to strength, the strength of the sample.

5. A method according to claim 4 wherein the rock sample is shale.

6. A method according to claim 4 wherein the pressure is an axial load of 1,000–10,000 psi and a confining stress of 500–9,000 psi.

7. A method according to claim 4 wherein said drilling fluid is mud.

8. A method according to claim 4 wherein said rock sample is prismatic-shaped.

* * * * *